United States Patent [19]

Schwender et al.

[11] Patent Number: 4,705,785

[45] Date of Patent: Nov. 10, 1987

[54] SUBSTITUTED THIACYCLOALKENO (3,2-B) PYRIDINES AND PHARMACEUTICAL COMPOSITIONS AND METHOD OF USE

[75] Inventors: Charles F. Schwender, Califon; John H. Dodd, Lebanon, both of N.J.

[73] Assignee: Ortho Pharmaceutical Corporation, Raritan, N.J.

[21] Appl. No.: 849,647

[22] Filed: Apr. 9, 1986

[51] Int. Cl.[4] ............... A61K 31/44; C07D 495/04
[52] U.S. Cl. ..................... 514/211; 514/212; 514/222; 514/231; 514/218; 540/544; 540/553; 540/597; 544/61; 544/127; 544/362; 546/114

[58] Field of Search ............... 546/114; 544/362, 61, 544/127; 540/544, 553, 597; 514/253, 211, 212, 301, 218, 222, 231

[56] References Cited

U.S. PATENT DOCUMENTS 4,285,955 8/1981 Egbert et al. .................. 546/257
4,532,248 7/1985 Franckowick et al. ............ 514/302

Primary Examiner—Henry R. Jiles
Assistant Examiner—Bernard I. Dentz
Attorney, Agent, or Firm—Benjamin F. Lambert

[57] ABSTRACT

Novel substituted thiacycloalkeno [3,2-b] pyridines are described. These compounds are useful as calcium channel antagonists with cardiovascular, antiasthmatic and antibronchoconstrictor activity.

23 Claims, No Drawings

SUBSTITUTED THIACYCLOALKENO (3,2-B) PYRIDINES AND PHARMACEUTICAL COMPOSITIONS AND METHOD OF USE

BACKGROUND OF THE INVENTION

1. Field of the Invention

This invention relates to certain substituted thiacycloalkeno [3,2-b] pyridines. These compounds are useful as calcium channel antagonists with cardiovascular, antiasthmatic, antibronchospastic, gastric antisecretory, cytoprotective and platelet aggregation inhibitory activity. This invention also relates to a process for preparing these compounds, compositions thereof, methods of use and novel intermediates.

2. Related Disclosure

U.S. Pat. No. 4,285,955 and U.S. Pat. No. 4,483,985 (which is a divisional of the aforementioned patent) disclose acyclic sulfone substitution on simple dihydropyridines which possess calcium channel antagonist activity. However, the compounds in question are chemically distinct from the compounds of the present invention.

10-Phenyl-2H-thiopyrano[3,2-b]quinolines are disclosed in G. P. A. Pagani, J. Chem. Soc., Perkin Trans. 2,1392-7(1974). However, these compounds are not calcium channel antagonists.

U.S. Pat. No. 4,532,248 discloses a broad genus of dihydropyridines including cyclic sulfones fused to a dihydropyridine nucleus. Cardiotonic activity is claimed for the entire genus. The compounds of the present invention, on the other hand, are potent calcium antagonists with pharmacologic activity opposite to that claimed in U.S. Pat. No. 4,532,248.

SUMMARY OF THE INVENTION

The substituted thiacycloalkeno [3,2-b] pyridines which are the subject of this invention have the following general formula.

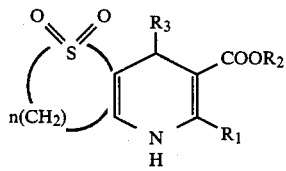

I wherein n is an integer from 1 to 12; $R_1$ is hydrogen, amino, alkyl, haloalkyl or $CH_2OR_2$; $R_2$ is straight chained or branched alkyl having 1 to 8 carbon atoms, cycloalkyl having 3 to 7 carbon atoms, or alkylene-X having at least 2 carbon atoms, wherein X is alkoxy, hydroxy, halo, p-tosyloxy, mesyloxy, amino or $-NR_4R_5$, wherein $R_4$ and $R_5$ are the same or different and are selected from hydrogen, alkyl, cycloalkyl, phenyl, benzyl, phenylethyl, or $R_4$, $R_5$ and the nitrogen atom to which they are attached form a 5, 6 or 7 membered heterocyclic ring which optionally contains an oxygen or sulfur atom or an additional nitrogen atom or said heterocyclic ring may be fused to a benzene ring, as in indoline, isoindoline, tetrahydroquinoline or tetrahydroisoquinoline, and in the instance wherein said heterocyclic ring is piperazino, said piperazino may optionally be substituted in the 4-position with the substituent $R_6$ which is selected from alkyl, cycloalkyl, benzyl, phenyl, or phenyl substituted by alkoxy, halo, alkyl, nitro or trifluoromethyl; $R_3$ is 2-pyridyl, 3- pyridyl, 3-pyridyl substituted at positions 2, 4, 5 or 6 with one or more groups selected from halogen, nitro, alkoxy, alkylthio, cyano, carbalkoxy, difluoromethoxy, difluoromethylthio or alkylsulfonyl; 2-thienyl, 3-thienyl, 2,1,3-benzoxadiazolyl, 2,1,3-benzthiadiazolyl or phenyl optionally substituted at positions 2 through 6 with one or more groups selected from hydrogen, alkyl, alkoxy, cyano, carbalkoxy, alkyl-thio, difluoromethoxy, difluoromethylthio, alkylsulfonyl, halo, nitro or trifluoromethyl; or the pharmaceutically acceptable acid addition salts thereof.

Also included in this invention is a process for preparing the compounds of formula I, said process being disclosed in detail hereinafter.

Also part of the present invention are certain intermediates and the process for the preparation thereof.

Preferred compounds of the present invention are:

1. Ethyl 2,3,4,7-tetrahydro-5-methyl-7-(3-nitrophenyl)-1,1-dioxothieno[3,2-b]pyridine-6-carboxylate.
2. N,N-Dimethylaminoethyl 2,3,4,7-tetrahydro-5-methyl-7-(3-nitrophenyl)-1,1-dioxothieno[3,2-b]pyridine-6-carboxylate.
3. N-Benzyl-N-methylaminoethyl 2,3,4,7-tetrahydro-5-methyl-7-(3-nitrophenyl)-1,1-dioxothieno[3,2-b]pyridine-6-carboxylate.
4. Ethyl 3,4,5,8-tetrahydro-6-methyl-8-(3-nitrophenyl)-1,1-dioxo-2H-thio-pyrano[3,2-b]pyridine-7-carboxylate.
5. N,N-Dimethylaminoethyl 3,4,5,8-tetrahydro-6-methyl-8-(3-nitrophenyl)-1,1-dioxo-2H-thiopyrano[3,2-b]pyridine-7-carboxylate.
6. N-Benzyl-N-methylaminoethyl 3,4,5,8-tetrahydro-6-methyl-8-(3-nitrophenyl)-1,1-dioxo-2H-thiopyrano[3,2-b]pyridine-7-carboxylate.
7. N-Benzyl-N-methylaminoethyl 3,4,5,8-tetrahydro-6-methyl-8-(2,3,4,5,6-pentafluorophenyl)-1,1-dioxo-2H-thiopyrano[3,2-b]pyridine-7-carboxylate.
8. Ethyl 9-(2,3,4,5,6-pentafluorophenyl)-2,3,4,5,6,9-hexahydro-7-methyl-1,1-dioxothiacyclohepteno[3,2-b]pyridine-8-carboxylate.
9. N-Benzyl-N-methylaminoethyl 2,4,5,6,9-hexahydro-7-methyl-9-(3-nitrophenyl)-1,1-dioxothiacycloheptena-[3,2-b]pyridine-8-carboxylate.
10. N,N-Dimethylaminoethyl 2,3,4,5,6,9-hexahydro-7-methyl-9-(3-nitrophenyl)-1,1-dioxothiacycloheptena[3,2-b]pyridine-8-carboxylate.
11. 2-Methoxyethyl 2,3,4,5,6,9-hexahydro-7-methyl-9-(3-nitrophenyl)-1,1-dioxo-thiacycloheptena[3,2-b]pyridine-8-carboxylate.
12. N-Benzyl-N-methylaminoethyl 9-(2,3,4,5,6-pentafluorophenyl)-2,3,4,5,6,9-hexahydro-7-methyl-1,1-dioxothiacycloheptena[3,2-b]pyridine-8-carboxylate.
13. Ethyl 10-(2,3,4,5,6-pentafluorophenyl)-3,4,5,6,7,10-hexahydro-8-methyl-1,1-dioxo-2H-thiacyclooctena[3,2-b]pyridine-9-carboxylate.
14. N-Benzyl-N-methylaminoethyl 10-(2,3,4,5,6-pentafluorophenyl)-3,4,5,6,7,10-hexahydro-8-methyl-1,1-dioxo-2H-thiacyclooctena[3,2-b]pyridine-9-carboxylate.
15. N-Benzyl-N-methylaminoethyl 3,4,5,6,7,10-hexahydro-8-methyl-10-(3-nitrophenyl)-1,1-dioxo-2H-thiacyclooctena[3,2-b]pyridine-9-carboxylate.
16. N-Benzyl-N-methylaminoethyl 11-(3-nitrophenyl) 2,3,4,6,7,8,11-octahydro-9-methyl-1,1-dioxothiacyclononena[3,2-b]pyridine-10-carboxylate.

The compounds of this invention are potent inhibitors of calcium ion uptake into smooth muscle tissue and act to relax or prevent contraction of tissue mediated by calcium mechanisms. The compounds of this invention have therapeutic utility in the treatment of cardiovascular disorders including hypertension, ischemia, angina, arrhythmias, congestive heart failure, peripheral vascular disorders such as intermittant claudication, migraines, myocardial infarction, platelet aggregation and stroke. In addition, the compounds of the invention possess utility with respect to other disorders such as hypersensitivity, allergy, asthma, dysmenorrhea, bronchoconstriction, esophageal spasm, premature labor and urinary tract, gastric hypersecretory and membrane integrity disorders. The compounds, compositions and methods for making the various aspects of the present invention will become more readily apparent from the following description.

DESCRIPTION AND PREFERRED EMBODIMENTS

Various terms used herein should be understood to signify the following:

Unless specified otherwise, the term "alkyl" refers to a straight or branched substituent consisting solely of carbon and hydrogen with no unsaturation and containing from 1 to 8 carbon atoms. The term "lower alkoxy" refers to a lower alkyl chain as described above having no more than 4 carbons. The term "halo" means fluoro, chloro, bromo and iodo.

The phrase "pharmaceutically acceptable salts" denotes salts of the free base which possess the desired pharmacological activity of the free base and which are neither biologically nor otherwise undesirable. These salts may be derived from inorganic or organic acids.

Examples of inorganic acids are hydrochloric acid, nitric acid, hydrobromic acid, sulfuric acid or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., aerosol, intravenous, sublingual, oral or topical. In preparing the compositions in oral dosage form, any of the usual pharmaceutical media may be employed, such as, for example, water, glycols, oils. alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case or oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. For aerosol use, suspensions or solutions may be employed. The pharmaceutical compositions will generally contain per dosage unit, e.g., tablet, capsule, powder, injection, teaspoonful and the like, from about 0.001 to about 100 mg/kg and preferably from about 0.001 to about 20 mg/kg of the active ingredient.

The novel compounds of the present invention may be synthesized according to the following reaction scheme wherein $R_1$, $R_2$, $R_3$, $R_4$, $R_5$, are as defined above, MCPBA signifies m-chloroperoxybenzoic acid, and Y is p-methylphenyl or alkyl.

Sulfones Synthesis

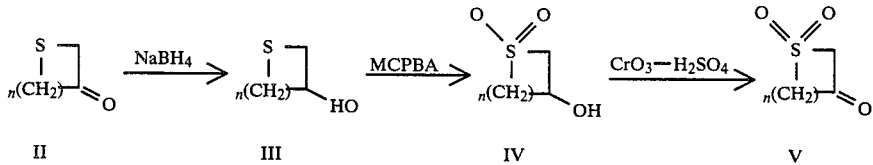

Synthetic Routes to Dioxothiacycloalkeno[3,2-b]pyridines

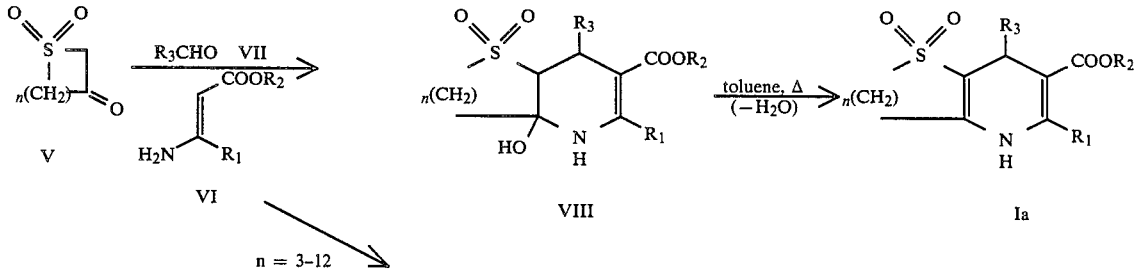

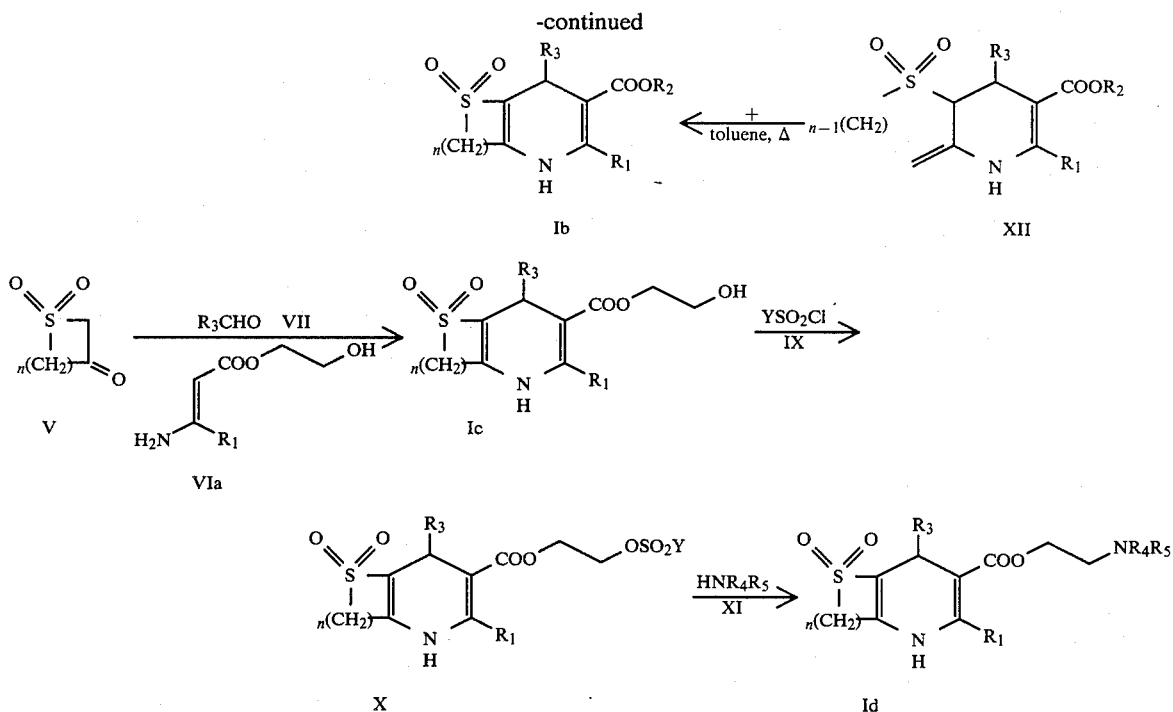

With reference to the above Reaction Scheme, the synthesis of the compounds of this invention is accomplished as follows:

The 3-keto cyclic sulfones of formula V (in the instance wherein n is 1–4) can be prepared in accordance with the procedure disclosed in B. Listert, P. Kuffner, and T. J. Arackel. Chem. Ber. 110, 1069–1085 (1977).

However, in the case of 3-oxo-tetrahydrothiophene-1,1-dioxide, that is wherein n is 2, the reference procedure is quite laborious. It has been found, in accordance with the present invention, that the compounds of formula V, in which n is 2 or 3, can be obtained in high yield in a straightforward manner from the respective 3-cyclic sulfides of formula II. Said compound of formula II may be prepared in accordance with the procedure disclosed in E. A. Fehnel, J. Amer. Chem. Soc. 74, 1569–74 (1952).

The 3-keto moiety of compound II is reduced to an alcohol (compound III) preferably with sodium borohydride although a number of other reducing agents such as diborane, lithium aluminum hydride or sodium cyanoborohydride may be used. Thereafter compound III is oxidized to compound IV preferably with m-chloroperoxybenzoic acid. Other suitable oxidizing agents are hydrogen peroxide or sodium periodate. Finally, the hydroxy moiety on compound IV is reoxidized to the corresponding keto moiety in compound V, preferably using Jones reagent (chromic anhydride in dilute sulfuric acid which is added to a solution of the alcohol in acetone). Other suitable oxidizing agents are: potassium dichromatic or Collins reagent (chromic anhydride in pyridine).

The 7, 8 and 9 membered 3-keto cyclic sulfones may be prepared in accordance with the method described in the Listert et al reference, previously mentioned.

Compounds of the formula I, wherein n is 1–12 (designated compound Ia in the following Reaction Scheme) may be prepared by stirring equal molar amounts of for example 3-oxotetrahydrothiophene-1,1-dioxide, the appropriately substituted aldehyde of formula VII and the substituted 3-aminoester of formula VI in ethanol for two to twenty-four hours at room temperature (see example 4). The resultant hydroxy intermediate of formula VIII is a novel compound. Said compound VIII is then heated in refluxing toluene for one to twenty-four hours to effect dehydration, thus producing compound Ia (see example 5).

The 6 to 15 membered cyclic sulfone products of formula I (wherein n is 3–12) may be obtained directly by refluxing a stirred ethanolic mixture of equimolar amounts of the ketosulfone of formula V, the aldehyde of formula VII and the substituted 3-aminoester of formula VI for about 16 hours in accordance with the procedure of example 6. The resultant product wherein n is 3–12, is designated compound Ib and/or XII. Note that compound Ib is actually the same as compound Ia, but obtained by a different route. Where the novel compound XII is formed, it can be converted to Ib by heating with ethanolic hydrogen chloride or toluene.

The preparation of compound I wherein $R_2$ is alkylene-$NR_4R_5$ can also be achieved when a compound of the formula V is reacted with an appropriate aldehyde of the formula VII and 2-hydroxyethyl-3-aminocrotonate of formula VIa in order to prepare the intermediate of formula Ic (see example VIII). The latter intermediate of formula Ic is then converted to the sulfonyl ester preferably by refluxing with a compound of the formula IX, wherein Y is p-methylphenyl or alkyl. The sulfonyl ester of formula X is then displaced with an appropriate amine of formula XI in order to produce a compound of the formula Id (see example 9).

In the following examples, both example 6 and example 10 illustrate the preparation of compound Ib, by the direct reaction of compound V, compound VII and compound VI, in the instance wherein n is 3–12. Various Reaction Schemes discussed above are disclosed in the following additional references:

G. A. Pagani, *J. Chem. Soc.*, Perkin Trans. 2, 1392–7 (1974).

K. G. Mason, M. A. Smith, and E. S. Stern, *J. Chem. Soc.* (C) 2171–76 (1967).

Maruko Seiyaku, Japan No. 58201764 (1984).

The following specific examples are illustrative of the present invention and should not be considered as limitative thereof in any manner.

EXAMPLES

Example 1

Tetrahydrothiopyran-3-ol

To a solution of tetrahydrothiopyran-3-one (ref 4) (10.0 g, 0.086 moles) in ethanol was added sodium borohydride (3.25 g, 0.086 moles) over a 5 minute period. After stirring for 30 minutes, a 1 N. solution of hydrochloric acid was added until a pH of 5 was reached. The reaction mixture was diluted with water and extracted with dichloromethane (6×50 mL). The organic phase was dried over magnesium sulfate, filtered, concentrated in vacuo, and distilled (approx. 100 torr, 158° C.) to give 6.8 g product. H' NMR $CDCl_3$ 3.9 (broad singlet, 1H) 2.2–2.9 (multiplet, 5H) 1.4–2.2 (multiplet, 4H).

Example 2

Tetrahydrothiopyran-3-ol-1,1-dioxide

A solution of tetrahydrothiopyran-3-ol (6.8 g, 0.58 moles) and chloroform (250 mL) was cooled to 0° C. and treated with m-chloroperoxybenzoic acid (23.4 g. 0.135 moles) at a rate which did not cause the temperature to rise above 10° C. After addition was complete, the thickened mixture was stirred at 0° C. for 1 hour and then at room temperature for 30 minutes. The resulting solid was removed by filtration and the filtrate evaporated in vacuo. The resulting solid was diluted with ethanol and evaporated in vacuo to remove remaining chloroform. The resulting solid was diluted with water (150 mL) and filtered. The filtrate was evaporated in vacuo and residual water was removed by repeated evaporation with toluene. This afforded 7.5 g of product as a colorless oil. H' NMR $D_6$-DMSO 4.3 (broad singlet, 1H) 3.4–4.0 (multiplet, 1H) 2.7–3.3 (multiplet, 4H) 1.2–2.1 (multiplet, 4H).

Example 3

Tetrahydrothiopyran-3-one-1,1-dioxide

To a solution of tetrahydrothiopyran-3-ol-1,1-dioxide (7.5 g, 0.05 moles) and acetone (150 mL) was slowly added enough Jones reagent to maintain a brown color for at least 10 minutes without need for additional reagent. The excess reagent was reduced by addition of isopropanol (5 mL). The mixture was filtered through anhydrous magnesium sulfate and the chromium salts were washed 3× with acetone. The solvent was removed in vacuo to give a solid which was triturated with ethanol. The resulting crystals were isolated by filtration and rinsed 3× with diethyl ether. After drying, 5.0 g of product was obtained. H' NMR $CDCl_3$ 4.0 (singlet, 2H) 3.3 (triplet, 2H) 2.6 (triplet, 2H) 2.3 (multiplet, 2H).

Example 4

Methyl 2,3,3a,4,7,7a-hexahydro-3a-hydroxy-5-methyl-7-(2-nitrophenyl)-1,1-dioxo-thieno[3,2-b]pyridine-6-carboxylate A solution of tetrahydrothiophene-3-oxo-1, 1-dioxide (1.3 g, 0.01 moles), 2-nitrobenzaldehyde (1.5 g, 0.01 moles) and methyl 3-aminocrotonate (1.1 g, 0.01 moles) in ethanol (20 mL) was stirred overnight. The resulting crystals were isolated by filtration and washed 2× with ethanol and 2× with diethyl ether. After drying under high vacuum for 24 hours 2.54 g of product was obtained, mp 175°–179° C. (dec).

Example 5

Methyl 2,3,4,7,-tetrahydro-5-methyl-7-(2-nitrophenyl)-1,1-dioxothieno [3,2-b]pyridine-6-carboxylate.

A mixture of methyl 2,3,3a,4,7,7a-hexahydro-3a-hydroxy-5-methyl-7-(2-nitrophenyl)-1,1-dioxothieno[3,2-b]pyridine-6-carboxylate (2.5 g, 0.0065 moles) and toluene (60 mL) was refluxed for 24 hours. The solvent was removed in vacuo and the resulting solid was recrystallized from ethanol. The crystals were washed with diethyl ether 2× and dried at 65° C. under high vacuum for 48 hours. This gave 1.78 g product; mp 215°–217° C.

Example 6

Methyl 3,4,5,8,-tetrahydro-6-methyl-8-(3-nitrophenyl)-1,1-dioxo-2H-thiopyrano-[3,2-b]pyridine-7-carboxylate A mixture of tetrahydrothiopyran-3-one-1, 1-dioxide (0.830 g, 0.0056 moles), 3-nitrobenzaldehyde (0.846 g, 0.0056 moles) and methyl 3-aminocrotonate (0.644 g. 0.0056 moles) in methanol (20 mL) was refluxed for 16 hours. After cooling, the resulting solid was isolated by filtration and washed with diethyl ether. This solid was dried at 40° C. for 4 hours under vacuum to give 0.620 g product; mp 236°–238° C.

Example 7

2-Hydroxyethyl 3-Aminocrotonate

Anhydrous ammonia gas was bubbled through a solution of 2-hydroxyethyl 3-oxo-butyrate (25 g, 0.17 moles) (ref 5) and ethanol (250 mL) for 20 minutes. This solution was stirred for 16 hours at room temperature. The solvent was removed in vacuo and the resulting oil was chromatographed on silica gel (250 g) using ethyl acetate-hexane 60:40 as eluant. The enriched fractions were combined and the solvent removed in vacuo to give the product; H' NMR $CDCl_3$ 4.33 (t, 2H) 3.85 (t, 2H) 3.55 (s, 1H) 2.85 (broad singlet, 1H) 2.31 (s, 3H).

Example 8

2-Hydroxyethyl 3,4,5,8-tetrahydro-6-methyl-8-(3-nitrophenyl)-1,1-dioxo-2H-thiopyrano [3,2-b]pyridine-7-carboxylate A mixture of tetrahydrothiopyran-3-one-1, 1-dioxide (2.80 g, 0.0189 moles), 3-nitrobenzaldehyde (2.85 g, 0.0189 moles), 2-hydroxyethyl-3-aminocrotonate (3.28 g, 0.0226 moles), ammonium acetate (0.291 g, 0.0038 moles) and ethanol (35 mL) was refluxed for 16 hours. After cooling to room temperature the resulting solid was isolated by filtration, washed with ethanol and diethyl ether. The product was dried under vacuum for 16 hours at room temperature affording the product; mp 233°–235° C.

Example 9

N-Benzyl-N-methyl-2-aminoethyl 2,3,4,8-tetrahydro-6-methyl-8-(3-nitrophenyl)-1,1-dioxo-5H-thiopyrano[3,2-b]pyridine-7-carboxylate Hemioxalate A mixture of 2-hydroxyethl 3,4,5,8-tetrahydro-6-methyl-8-(3-nitrophenyl)-1,1-dioxo-2H-thiopyrano[3,2-b]pyridine-7-carboxylate (2.5 g 0.0061 moles), p-toluenesulfonyl chloride (4.65 g, 0.0244 moles), triethylamine (2.46 g, 0.0244 moles) and dichloromethane (25 mL) was refluxed for 4.5 hours. The reaction mixture was cooled and the solvent removed in vacuo. The resulting oil was chromatographed on silica gel (170 g) using ethyl acetate - methanol 95:5 as eluant. The enriched fractions containing the tosylate (H' NMR CDCl$_3$ 7.3–8.2 (multiplet, 8H) 6.9 (singlet, 1H) 5.2 (singlet, 1H)) were combined and N-benzyl-N-methylamine (4.69 g, 0.0387 moles) was added to the solution. The solvent was removed in vacuo and the resulting residue was allowed to stand for 72 hours at room temperature. Chromatography of the mixture was accomplished on silica gel (170 g) using a mixture of ethyl acetate and methanol 97:3 as eluant. The isolated product was dissolved in ether and treated with a saturated solution of oxalic acid in diethyl ether. The resulting solid was collected by filtration, washed with diethyl ether and dried at 60° C. for 16 hours under vacuum affording the product (2.07 g) mp 220°–222° C.

Example 10

Ethyl 2,3,4,5,6,9-hexahydro-7-methyl-9-(3-nitrophenyl)-1,1-dioxothiacyclohepteno[3,2-b]pyridine-8-carboxylate A solution of thiacycloheptane -3-one-1, 1-dioxide (1.3 g, 0.0080 moles), 3-nitrobenzaldehyde (1.2 g, 0.0080 moles), ethyl 3-aminocrotonate (1.04 g, 0.0080 moles) and ethanol (20 mL) was refluxed 16 hours. After removal of the solvent in vacuo the residue was chromatographed on silica gel (170 g) using a mixture of ethyl acetate and hexane (4:1) as eluant. The enriched fractions were combined and the solvent removed in vacuo. The solid was triturated with diethyl ether, filtered and dried under vacuum overnight to give 1.52 g of product; mp 211°–213° C.

Example 11

Ethyl 3,4,5,7,10,10a-hexahydro-8-methyl-10-(3-nitrophenyl)-1,1-dioxo-2H-thiacyclooecteno[3,2-b]pyridine-9-carboxylate A solution of thiacyclooctane -3-one-1, 1-dioxide (0.35g, 0.002 moles), 3-nitrobenzaldehyde (0.30 g, 0.002 moles), ethyl 3-aminocrotonate (0.26 g, 0.002 moles) and ethanol (30 mL) was refluxed 16 hours. After cooling to room temperature a yellow precipitate formed which was isolated by filtration, washed with diethyl ether and dried in vacuo to afford the product (0.56g) mp 211°–214° C.

Example 12

Ethyl 3,4,5,6,7,10-hexahydro-8-methyl-10-(3-nitrophenyl-1,1-dioxo-2H-thiacycloocteno[3,2-b] pyridine-9-carboxylate A mixture of ethyl 3,4,5,7,10a-hexahydro-8-methyl-10-(3-nitrophenyl)-1,1-dioxo-2H-thiacyclooecteno[3,2-b]pyridine-9-carboxylate (0.45 g, 0.0011 moles) and toluene (30 mL) was refluxed for 24 hours. The resulting solid was isolated by filtration, washed with diethyl ether and dried in vacuo to afford the product mp 234°–235° C.

The compounds of the present invention were evaluated for their biological properties. The present compounds have shown the ability to influence calcium mediated events including inhibition of smooth muscle contraction of trachea and vascular tissues. The model screening regimen used to evaluate these compounds has shown:

(1) Inhibition of nitrendipine binding to calcium channels.
(2) Ability to modulate the activity of tissues which are dependent on calcium utilization as in trachea and vascular tissue,
(3) Their use as antihypertensives and/or bronchodilating agents in mammals.

Based on the above results, it is believed that these compounds will be useful in hypertension, myocardial, ischemia, angina, congestive heart failure, migraine, myocardial infarction, platelet aggregation, stroke, hypersensitivity, allergy, asthma, gastric secretory dysmenorrhea, esophageal spasm, premature labor and urinary tract disorders.

The following Table 1 sets forth inhibition of nitrendipine binding as well as inhibition of calcium dependent smooth muscle contraction in terms of percent inhibition, for a number of representative compounds of the present invention.

TABLE I

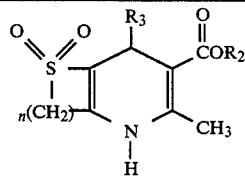

| N | R$_2$ | R$_3$ | mp °C. | Inhibition of Nitrendipine binding IC$_{50}$ (μM) | Inhibition of Ca$^{2+}$ dependent smooth muscle contraction % inhibition | (μM) concentration |
|---|-------|-------|--------|-------|-------|-------|
| 2 | CH$_3$ | C$_6$F$_5$ | 228–231 | 0.15 | 47 | 2.0 |

TABLE I-continued

[Structure: dihydropyridine with SO₂-(CH₂)ₙ ring, R₃, COR₂, CH₃, NH]

| N | R₂ | R₃ | mp °C. | Inhibition of Nitrendipine binding IC₅₀ (μM) | Inhibition of Ca²⁺ dependent smooth muscle contraction % inhibition | (μM) concentration |
|---|---|---|---|---|---|---|
| 2 | CH₃ | 3-NO₂—C₆H₄ | 198–201 | 0.70 | 76 | 10.0 |
| 2 | CH₃ | 3-Cl—C₆H₄ | 196–199 | 0.93 | — | — |
| 2 | CH₃ | 3-CH—C₆H₄ | 204–205 | 2.0 | — | — |
| 2 | CH₃ | 2-NO₂—C₆H₄ | 215–217 | 1.35 | 63 | 2.0 |
| 2 | CH₂CH₂NCH₃CH₂C₆H₅ | 3-NO₂—C₆H₄ | 117–123 | 1.0 | 65 | 5.0 |
| 3 | CH₂CH₃ | 2-NO₂—C₆H₄ | 215–217 | 1.5 | 75 | 10.0 |
| 3 | CH₂CH₃ | 3-NO₂—C₆H₄ | 207–209 | 0.17 | 69 | 10.0 |
| 3 | CH₃ | 3-NO₂—C₆H₄ | 236–238 | 0.16 | 57 | 10.0 |
| 3 | CH₃ | 2-NO₂—C₆H₄ | 291–292 | 0.89 | 84 | 10.0 |
| 3 | CH₂C₆H₅ | 2-NO₂—C₆H₄ | 123–126 dec | 3.4 | 69 | 10.0 |
| 3 | CH₃ | C₆F₅ | 242–244 | 0.40 | 46 | 0.5 |
| 3 | CH₂CH₂NCH₃CH₂C₆H₅ | 3-NO₂—C₆H₄ | 220–222 | 1.85 | 46 | 2.0 |
| 4 | CH₃ | 3-NO₂—C₆H₄ | 217–219 | 0.027, 0.039 | 94 | 2.0 |
| 2 | CH₂CH₃ | C₆F₅ | 223–226 | 0.56 | 48 | 2.0 |
| 4 | CH₂CH₃ | C₆F₅ | 202–205 | 0.028 | 95 | 0.5 |
| 4 | CH₂CH₂NCH₃CH₂C₆H₅ | C₆F₅ | 160–165 | 0.035 | 74 | 0.2 |
| 4 | CH₂CH₃ | 3-NO₂—C₆H₄ | 211–213 | 0.044 | 96 | 2.0 |
| 4 | CH₂CH₂NCH₃CH₂C₆H₅ | 3-NO₂—C₆H₄ | 123–127 | 0.13 | 68 | 0.2 |
| | [structure with 2-NO₂-C₆H₄, CO₂CH₃, OH, CH₃, NH, SO₂ ring] | | 175–179 dec | 56% @ 8.0 | 26 | 2.0 |
| | [structure with 3-NO₂-C₆H₄, CO₂CH₂CH₃, CH₃, NH, SO₂ ring] | | 211–214 | 0.27 | 53% | 2.0 |
| 5 | —CH₂CH₃ | 3-NO₂—C₆H₄ | 234–235 | 0.0055 | 71% | 0.1 |

The assay for inhibition of nitrendipine binding follows the following procedure:

Female, New Zealand white rabbits (1–2 kg) are sacrificed by cervical dislocation, and the heart is immediately removed, cleaned, and chopped into small pieces. The tissue is homogenized in 5× volume of 0.05M Hepes buffer, pH 7.4. The homogenate is centrifuged at 4000 xg for 10 minutes; the supernatant is recentrifuged at 42,000 xg for 90 minutes. The resulting membrane pellet is resuspended (0.7 ml/g weight) in 0.05M Hepes, pH 7.4 and stored at −70° C. until used. Each tube of the binding assay contains ³H-nitrendipine (0.05–0.50nM), buffer, membranes (0.10 ml), and test compound in a total volume of 1.0 ml. After 90 minutes at 4° C., the bound nitrendipine is separated from the unbound by filtration on Whatman GF/C fibers. After rinsing, the filters are dried and counted in a liquid scintillation counter.

Non-specific binding of ³H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be obtained.

The test for inhibition of calcium dependent smooth muscle contraction is determined according to the following procedure:

Trachea from dogs sacrificed by excess KCI injection are stored overnight at 4° C. in oxygenated Krebs-Henseleit buffer. Tracheal rings, one cartilage segment wide (5-10 mm), are cut starting from the bronchial end. After cutting the cartilage, the trachealis muscle tissue is suspended in oxygenated Krebs-henseleit buffer at 37° C. in a 25 ml tissue bath. After a 60 minutes equilibration period, the tissues are challenged with 10 uM carbachol. After 5 minutes the tissues are rinsed and allowed to rest 50 minutes. The tissues are then challenged with 50 mM KCl and, after 30 minutes, the contractions are quantitated. The tissues are then rinsed and reequilibrated for 50 minutes. Test compounds are then added for 10 minutes, and the tissue is rechallenged with 50 mMKcl. After 30 minutes, the contraction is recorded and used to determine the % inhibition of control.

The percent inhibition of smooth muscle contraction is calculated from response data before and after drug treatment.

$$\% \text{ inhibition} = 100 - 100 \left( \frac{\text{peak response after drug treatment}}{\text{peak response before drug treatment}} \right)$$

A rating is assigned to the compound depending upon the percent inhibition obtained.

We claim:

1. A compound of the formula

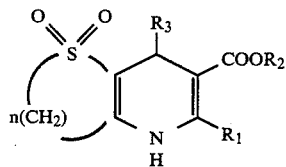

I wherein n is an integer from 1 to 12; $R_1$ is hydrogen, amino, alkyl, haloalkyl or $CH_2OR_2$; $R_2$ is straight chained or branched alkyl having 1 to 8 carbon atoms, cycloalkyl having 3 to 7 carbon atoms, or alkylene-X having at least 2 carbon atoms, wherein X is alkoxy, hydroxy, halo, p-tosyloxy, mesyloxy, amino or —$NR_4R_5$, wherein $R_4$ and $R_5$ are the same or different and are selected from hydrogen, alkyl, cycloalkyl, phenyl, benzyl, phenylethyl, or $R_4$, $R_5$ and the nitrogen atom, to which they are attached form a 5, 6 or 7 membered heterocyclic ring which optionally contains an oxygen or sulfur atom or an additional nitrogen atom, or said heterocyclic ring may be fused to a benzene ring to form an indoline, isoindoline, tetrahydroquinoline or tetrahydroisoquinoline group, and in the instance wherein said heterocyclic ring is piperazino, said piperazino may optionally be substituted in the 4-position with the substituent $R_6$ which is selected from alkyl, cycloalkyl, benzyl, phenyl, or phenyl substituted by alkoxy, halo, alkyl, nitro or trifluoromethyl; $R_3$ is 2-pyridyl, 3-pyridyl, 3-pyridyl substituted at positions 2, 4, 5 or 6 with one or more groups selected from halogen, nitro, alkoxy, alkylthio, cyano, carbalkoxy, difluoromethoxy, difluoromethylthio or alkylsulfonyl; 2-thienyl, 3-thienyl, 2,1,3-benzoxadiazolyl, 2,1,3-benzthiadiazolyl or phenyl optionally substituted at positions 2 through 6 with one or more groups selected from hydrogen, alkyl, alkoxy, cyano, carbalkoxy, alkylthio, difluoromethoxy, difluoromethylthio, alkylsulfonyl, halo, nitro or trifluoromethyl; or the pharmaceutically acceptable acid and base addition salts thereof wherein alkyl all occurrences is of one to eight carbon atoms.

2. A compound of claim 1 which is ethyl 2,3,4,7-tetrahydro-5-methyl-7-(3-nitrophenyl)-1,1-dioxothieno pyridine-6-carboxylate.

3. A compound of claim 1 which is N,N-dimethylaminoethyl 2,3,4,7-tetrahydro-5-methyl-7-(3-nitrophenyl)-1,1-dioxothieno-pyridine-6-carboxylate.

4. A compound of claim 1 which is N-benzyl-N-methylaminoethyl 2,3,4,7-tetrahydro-5-methyl-7-(3-nitrophenyl)-1,1-dioxothienopyridine-6-carboxylate.

5. A compound of claim 1 which is ethyl 3,4,5,8-tetrahydro-6-methyl-8-(3-nitrophenyl)-1,1-dioxo-2H-thiopyranopyridine-7-carboxylate.

6. A compound of claim 1 which is N,N-dimethylaminoethyl 3,4,5,8-tetrahydro-6-methyl-8-(3-nitrophenyl)-1,1-dioxo-2H-thiopyrano pyridine-7-carboxylate.

7. A compound of claim 1 which is N-benzyl-N-methylaminoethyl 3,4,5,8-tetrahydro-6-methyl-8-(3-nitrophenyl)-1,1-dioxo-2H-thiopyranopyridine-7-carboxylate.

8. A compound of claim 1 which is N-benzyl-N-methylaminoethyl 3,4,5,8-tetrahydro-6-methyl-8-(2,3,4,5,6-pentafluorophenyl)-1,1-dioxo-2H-thiopyrano-yyridine-7-carboxylate.

9. A compound of claim 1 which is ethyl 9-(2,3,4,5,6-pentafluorophenyl)-2,3,4,5,6,9-hexahydro-7-methyl-1,1-dioxothiacyclohepteno pyridine-8-carboxylate.

10. A compound of claim 1 which is N-benzyl-N-methylaminoethyl 2,4,5,6,9-hexahydro-7-methyl-9-(3-nitrophenyl)-1,1-dioxothiacyclohepteno pyridine-8-carboxylate.

11. A compound of claim 1 which is N, N-dimethylaminoethyl-2,3,4,5,6,9-hexahydro-7-methyl-9-(3-nitrophenyl)-1,1-dioxothiacyclohepteno pyridine-8-carboxylate.

12. A compound of claim 1 which is 2-methoxyethyl 2,3,4,5,6,9-hexahydro-7-methyl-9-(3-nitrophenyl)-1,1-dioxo-thiacyclohepteno pyridine-8-carboxylate.

13. A compound of claim 1 which is N-benzyl-N-methylaminoethyl 9-(2,3,4,5,6-pentafluorophenyl)-2,3,4,5,6,9-hexahydro-7-methyl-1,1-dioxothiacyclohepteno pyridine-8-carboxylate.

14. A compound of claim 1 which is ethyl 10-(2,3,4,5,6-pentafluorophenyl)-3,4,5,6,7,10-hexahydro-8-methyl-1,1-dioxo-2H-thiacyclooocteno pyridine-9-carboxylate.

15. A compound of claim 1 which is N-benzyl-N-methylaminoethyl 10-(2,3,4,5,6-pentafluorophenyl)-3,4,5,6,7,10-hexahydro-8-methyl-1,1-dioxo-2H-thiacyclooocteno pyridine-9-carboxylate.

16. A compound of claim 1 which is N-benzyl-N-methylaminoethyl 3,4,5,6,7,10-hexahydro-8-methyl-10-(3-nitrophenyl)-1,1-dioxo-2H-thiacyclooocteno pyridine-9-carboxylate.

17. A calcium channel antagonist composition comprising an inert carrier and as an active ingredient, an effective calcium channel antagonist amount of the compound of claim 1.

18. The calcium channel antagonist composition of claim 17, wherein said active ingredient consists of N-benzyl-N-methylaminoethyl 9-(2,3,4,5,6-pentafluorophenyl)-2,3,4,5,6,9-hexahydro-7-methyl-1,1-dioxothiacyclohepteno pyridine-8-carboxylate.

19. A pharmaceutical composition useful as a calcium channel antagonist in unit, topical, oral, sublingual, aerosol and intravenous dosage forms, comprising from about 0.001 mg./kg. to about 100 mg./kg. of the compound of claim 1 in admixture with a pharmaceutically-acceptable carrier.

20. The composition of claim 25, comprising from about 0.001 mg./kg. to about 20 mg./kg. of the compound of claim 1, in admixture with the pharmaceutically acceptable carrier.

21. A method for treating myocardial insufficiencies including angina, vasospasm or infarction, comprising administering to a mammal a pharmaceutical composition according to claim 19.

22. A method for treating cardiovascular disorders including hypertension, migraine, stroke or platelet aggregation, comprising administering to a mammal a pharmaceutical composition according to claim 19.

23. A method for treating allergies, hypersensitivities, asthma and bronchospastic disorders comprising administering to a mammal a pharmaceutical composition according to claim 19.

* * * * *

UNITED STATES PATENT AND TRADEMARK OFFICE
CERTIFICATE OF CORRECTION

PATENT NO. : 4,705,785
DATED : November 10, 1987
INVENTOR(S) : Charles F. Schwender, John L. Dodd It is certified that error appears in the above-identified patent and that said Letters Patent is hereby corrected as shown below:

Claim 20, line 5:
    Delete "25" and substitute therefor -19-

Claims 2-18 and throughout the specification, where appropriate, [3,2-b] should appear before -pyridine- Claim 8, line 4:
    Delete "yyridine" and substitute therefor -pyridine- Signed and Sealed this Nineteenth Day of July, 1988

Attest:

DONALD J. QUIGG

Attesting Officer     Commissioner of Patents and Trademarks